United States Patent [19]

Falling et al.

[11] Patent Number: 5,103,028

[45] Date of Patent: Apr. 7, 1992

[54] PROCESS FOR THE PREPARATION OF 3,4-DIHALO-1,2-EPOXYBUTANES

[75] Inventors: Stephen N. Falling; Patricia Lopez-Maldonado, both of Kingsport, Tenn.

[73] Assignee: Eastman Kodak Company, Rochester, N.Y.

[21] Appl. No.: 756,687

[22] Filed: Sep. 9, 1991

[51] Int. Cl.$^5$ .................. C07D 301/00; C07D 303/08
[52] U.S. Cl. ........................ 549/540; 549/563
[58] Field of Search .......................... 547/540

[56] References Cited

U.S. PATENT DOCUMENTS 3,510,532  5/1970  Caropreso et al. ............... 544/540
4,116,984  9/1978  Prinzbach et al. ............... 549/540

FOREIGN PATENT DOCUMENTS 1079206  8/1967  United Kingdom ............... 549/540

OTHER PUBLICATIONS

Shellhamer et al., *J. Heterocyclic Chem.*, 20, pp. 229–232 (1983).
Chemical Abstracts 82:86251k [Movsumzade et al., Dokl. Akad. Nauk. Az. SSR, 30, 14 (1974)].

*Primary Examiner*—J. E. Evans
*Attorney, Agent, or Firm*—J. Frederick Thomsen; William P. Heath, Jr.

[57] ABSTRACT

Disclosed is a process for the preparation of 3,4-dichloro- and 3,4-dibromo-1,2-epoxybutane by the reaction of 3,4-epoxy-1-butane with chlorine or bromine in the presence of a quaternary ammonium or phosphonium halide compound. The reaction preferably is carried out by the addition of 3,4-epoxy-1-butane and chlorine or bromine to an organic, halogenation solvent containing chlorine or bromine and the quaternary compound.

6 Claims, No Drawings

PROCESS FOR THE PREPARATION OF 3,4-DIHALO-1,2-EPOXYBUTANES

This invention pertains to the preparation of 3,4-dihalo-1,2-epoxybutanes by the reaction of chlorine or bromine with 3,4-epoxy1-butene. More specifically, this invention pertains to the chlorination or bromination of 3,4-epoxy-1-butene in the presence of an inert solvent and a quaternary ammonium or phosphonium halide.

The literature contains a number of references to the preparation of 3,4-dichloro-1,2-epoxybutane. British Patent 864,880 describes the synthesis of 3,4 dichloro 1,2 epoxybutane by the dehydrochlorination of 1,3,4-trichloro-butan-2-ol. The preparation of 3,4-dichloro-1,2-epoxybutane by the oxidation of 3,4-dichloro-1-butene with peracetic or performic acid is described in British Patent 784,620 and U.S. Pat. No. 3,150,154 and by Hawkins, *J. Chem. Soc.*, 1959, 248. The preparation of 3,4-dichloro-1,2 epoxybutane by the addition of liquid chlorine to undiluted 3,4-epoxy-1-butene at −30° C. is disclosed by Movsumzade et al, Dokl. Akad. Nauk. Az. SSR, 30, 14 (1974); Chem. Abstr. 82:86251k.

A study of the ionic and free radical halogenation of 3,4-epoxy-1-butene is reported by Shellhamer et al, *J. Heterocyclic Chem.*, 20, 229 (1983) although the procedures used in this mechanistic study are not practical for the preparation of 3,4-dichloro-1,2-epoxybutane on a commercial scale. For example, Shellhamer et al performed their reactions at very low concentrations and allowed the reactions to proceed to only 20 to 50% of completion. Furthermore, the products were purified by gas chromatography and were described as being unstable liquids which turn light yellow after several days.

We chlorinated 3,4-epoxy1-butene according to a conventional halogenation procedure by adding a slight stoichiometric excess of chlorine to a 12% solution of 3,4-epoxy1-butene in dichloromethane at −5° to 5° C. Although 3,4-dichloro-1,2-epoxybutane was obtained, about 50% of the 3,4-epoxy-1-butene was converted to high boiling, oligomeric compounds. When the crude product was distilled, 3,4-dichloro-1,2-epoxybutane was obtained in a yield of only 6.5%.

We have discovered that 3,4-dichloro and 3,4-dibromo-1,2-epoxybutanes may be conveniently prepared in good yields and high purity by the reaction of 3,4-epoxy 1-butene and chlorine or bromine in the presence of a quaternary ammonium or phosphonium halide. The present invention therefore provides a process for the preparation of a compound having the formula

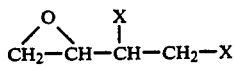

which comprises reacting 3,4-epoxy-1-butene with $X_2$ in the presence of a quaternary nitrogen or phosphorus onium halide compound having the formula

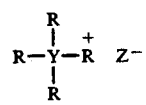

wherein each R is a hydrocarbyl group; X is Cl or Br; Y is a nitrogen or phosphorus atom; and Z is halogen such as Cl, Br and I. The process may be carried out in the presence of a conventional halogenation solvent.

The tetrahydrocarbylammonium and tetrahydrocarbylphosphonium halide compounds may contain a total of 4 to about 60 carbon atoms, preferably about 8 to 32 carbon atoms, provided, of course, that the onium halide compound exhibits sufficient solubility in the particular halogenation solvent used. When using one of the preferred halogenation solvents such as a chlorinated hydrocarbon, the onium halides which are particularly preferred are the tetra-n-butylphosphonium halides and the tetraethylammonium halides. These specific onium halides are sufficiently soluble in the preferred halogenation solvents to enable their use in catalytically effective amounts and are sufficiently water soluble to permit their removal by water washing the 3,4-dihalo-1,2-epoxybutane product. However, it may be possible to utilize the 3,4-dihalo-1,2-epoxybutane product without the removal of the onium halide catalyst. The halide anion Z of the onium halides normally is the same as the halogen $X_2$ used in the process. The catalytically effective amount of the onium halide compound typically is in the range of about 0.001 to 0.1 moles per liter of halogenation solvent.

The organic, halogenation solvent normally used in the process of the present invention may be selected from various aliphatic, cycloaliphatic and aromatic hydrocarbons and halogenated derivatives thereof. Halogenated hydrocarbons, such as chlorinated alkanes and halobenzenes, e.g., dichloromethane, chloroform, carbon tetrachloride, 1,2-dichloroethane, tetrachloroethylene, 1,1,1-trichloroethane, chlorobenzene and the isomers of di- and tri-chlorobenzene, are preferred since non halogenated hydrocarbons may result in product of lower quality and halogenation of the solvent during the process. The use of catalyst/solvent combinations comprising (1) tetra-n-butylphosphonium chloride or bromide with chlorobenzene or dichloromethane and (2) tetraethylammonium chloride or bromide with dichloromethane are particularly preferred.

The halogenation process in general may be carried out at a temperature of about −10° to 70° C. When 3,4-epoxy-1-butene is chlorinated according to our invention, a reaction temperature of about 0° to 20° C. is preferred whereas a range of about 20° to 50° C. is preferred for bromination.

A preferred embodiment of the present invention concerns the addition of 3,4-epoxy-1-butene to a solution of chlorine or bromine and a quaternary ammonium or phosphonium halide, preferably chloride or bromide, in an organic, halogenation solvent. At the commencement of the operation of the process, the halogenation solvent contains dissolved chlorine or bromine and then chlorine or bromine and 3,4-epoxy-1-butene are added at rates or in increments which maintain dissolved chlorine or bromine in the reaction mixture. At the end of a production run or cycle, the addition of chlorine is stopped and 3,4-epoxy-1-butene may be added to consume all of the dissolved chlorine or bromine or unreacted halogen may be removed by distillation or by washing with aqueous sodium thiosulfate.

The preferred embodiment described hereinabove comprises a process for the preparation of a compound having the formula

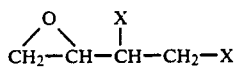

which comprises adding 3,4-epoxy-1-butene and $X_2$ to a solution of $X_2$ and a quaternary nitrogen or phosphorus onium halide compound having the formula

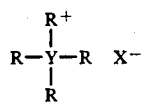

in an organic, halogenation solvent, wherein each R is a hydrocarbyl group; X is Cl or Br; and Y is a nitrogen or phosphorus atom. As mentioned above, the 3,4-epoxy-1-butene and halogen $X_2$ may be added simultaneously or intermittently and/or separately to maintain dissolved halogen in the reaction during most of the process time. The presence of dissolved halogen is evident from the color of the reaction mixture; a light green for chlorine and a light orange for bromine. At the conclusion of the process, the mixture is given an aqueous work up to remove catalyst and excess halogen.

The halogenation process of the present invention is further illustrated by the following examples. Gas chromatographic (GC) analyses (reported in area percent) were performed on a Hewlett Packard 5890A gas chromatograph with a 30 meter DB5 0.32 mm inside diameter capillary column with a 0.25 micron film thickness. The temperature program was 35° C. (4.5 minutes), 20° C. per minute to 280° C., hold 5 minutes. The structures of the products obtained were confirmed by nuclear magnetic and mass spectrometry.

EXAMPLE 1

A 3000-mL, three neck flask was equipped with a gas addition tube, condenser, thermometer, mechanical stirrer, a line for feeding 3,4-epoxy-1-butene from a metering pump, and a cooling bath. To the flask was added 6.25 g (0.0377 mole) of tetraethylammonium chloride and 1250 mL of dichloromethane. The solution was cooled to 10°–20° C. then the chlorine gas addition was begun. After the solution had turned light green, the 3,4-epoxy-1-butene and chlorine were added simultaneously over about 50 minutes at 10°–20° C. A total of 250 mL of 3,4-epoxy-1-butene was pumped into the mixture at about 5 mL per minute and the chlorine addition was controlled so as to keep the solution green in color. After 250 mL of 3,4-epoxy-1-butene had been added, the chlorine addition was stopped and more 3,4-epoxy-1-butene was added as needed to decolorize the solution. A total of 139.5 g (3.103 moles) chlorine and 222.6 g (3.176 moles) of 3,4-epoxy-1-butene was added. The mixture was washed twice with 1200 mL of water then once with 600 mL of aqueous sodium bicarbonate (300 mL of saturated aqueous sodium bicarbonate plus 300 mL of water). The mixture was dried with anhydrous magnesium sulfate and filtered and the solvent was removed from the filtrate by vacuum rotary evaporation (up to about 50° C. and about 30 torr). The crude yellow product (572.63 g) was vacuum distilled at 7 torr to give 3,4-dichloro-1,2-epoxybutene at 64°–66° C. The colorless liquid weighed 365.66 g (theory 447.80 g, 81.7%) and had a GC assay of 99.3% (59.6/40.4 mixture of diastereomers).

EXAMPLE 2

A 2000-mL, four neck flask was equipped with an addition funnel for addition of bromine, condenser, thermometer, mechanical stirrer, and a line for feeding 3,4-epoxy-1-butene from a metering pump. To the flask was added 3.01 g (0.0143 mole) of tetraethylammonium bromide and 600 mL of dichloromethane and the slow addition of bromine was begun at room temperature. After the solution had turned light orange, the 3,4-epoxy-1-butene and bromine were added simultaneously over about 90 minutes. The solution temperature was allowed to rise during the reaction (25°–42° C.). The 3,4-epoxy-1-butene was pumped into the mixture at about 2.4 mL per minute and the bromine addition was controlled so as to keep the solution orange in color. A total of 235.7 g (1.475 moles) of bromine and 91.91 g (1.311 moles) of 3,4-epoxy-1-butene was added. The orange solution was decolorized by washing twice with 300 mL of 10% aqueous sodium thiosulfate, then it was washed twice with 300 mL of water and once with 300 mL of half saturated, aqueous sodium bicarbonate (150 mL of saturated aqueous sodium bicarbonate plus 150 mL of water). The mixture was dried with anhydrous magnesium sulfate and filtered and the solvent was removed by vacuum rotary evaporation (up to about 50° C. and about 30 torr). The crude yellow product was vacuum distilled at 1.4–2.1 torr to give 3,4-dibromo-1,2-epoxybutane at 61°–65° C. The colorless liquid weighed 273.33 g (theory 301.47 g, 90.7%) and had a GC assay of 99.5% (47.7/52.3 mixture of diastereomers).

EXAMPLE 3

To a 3000-mL, three neck flask equipped with a gas addition tube, condenser, thermometer, mechanical stirrer, a line for feeding 3,4-epoxy-1-butene from a metering pump, and cooling bath was added 600 mL of chlorobenzene and 4.75 g (19.0 millimole) of tetra-n-butylphosphonium chloride. Chlorine gas addition was begun after the solution was cooled to 10° C. After the solution had turned light green, the 3,4-epoxy-1-butene and chlorine were added simultaneously over about 50 minutes at 10 20° C. The 3,4-epoxy-1-butene (130 mL) was pumped into the mixture at about 2.5 mL/minute and the chlorine addition was controlled so as to keep the solution green in color. After 130 mL of 3,4-epoxy-1-butene had been added, the chlorine addition was stopped and more 3,4-epoxy-1-butene was added as needed to decolorize the solution. A total of 128.2 g (1.808 moles) chlorine and 117.2 g (1.672 moles) of 3,4-epoxy-1-butene was added. The mixture was washed twice with 300 mL of water then once with 300 mL of half saturated, aqueous sodium bicarbonate. The mixture was dried, filtered, and distilled at 100 torr through a 12-inch Hastalloy C packed column to give a product fraction of 3,4-dichloro-1,2-epoxybutane at 121°–127° C. The colorless liquid weighed 167.1 g (theory 235.8 g, 70.9%) and had a GC assay of 97.5%.

EXAMPLE 4

To a 500-mL, four neck flask equipped with a gas addition tube, condenser, thermometer, mechanical stirrer, addition funnel, and cooling bath was added 200 mL of dichloromethane and 1.00 g (6.04 millimole) of tetraethylammonium chloride. The solution was cooled to −5° to 5° C. and then the addition of chlorine gas was begun. After the solution had turned light green, 39.7 g (0.560 mole) of chlorine and 34.8 g (0.497 mole) of 3,4-epoxy-1-butene were added simultaneously over about 60 minutes at −5° to 5° C. so as to keep the solution green in color. The mixture was washed with 100 mL of 10% aqueous sodium thiosulfate then with 100 mL of half saturated, aqueous sodium bicarbonate. The mixture was dried, filtered, and concentrated. The crude product was distilled at 7 torr to give a product fraction of 3,4 dichloro 1,2 epoxybutane at 58°–60° C. The colorless liquid weighed 56.8 g (81.1% of theory) and had a GC assay of 99.3%.

EXAMPLE 5

To a 500-mL, four neck flask equipped with a gas addition tube, condenser, thermometer, mechanical stirrer, and cooling bath was added 200 mL of dichloromethane, 34.8 g (0.497 mole) of 3,4-epoxy-1-butene and 1.00 g (6.04 mmole) of tetraethylammonium chloride. The solution was cooled to −5° to 5° C. and then the chlorine gas addition was begun. Chlorine (39.5 g, 0.557 mole) was added at −5° to 5° C. until the solution turned green. The mixture was washed with 100 mL of 10% aqueous sodium thiosulfate then 100 mL of half saturated, aqueous sodium bicarbonate. The mixture was dried, filtered, and concentrated. The crude product was distilled at 7 torr to give a product fraction of 3,4-dichloro-1,2-epoxybutane at 67°–70° C. The colorless liquid weighed 46.2 g (66.0%) and had a GC assay of 98.5%.

EXAMPLE 6

The procedure of Example 5 was repeated using tricaprylmethylammonium chloride (3.0 g, 7.4 millimole) instead of tetraethylammonium chloride as catalyst. The distilled 3,4-dichloro-1,2-epoxybutane product (bp 58°–60° C., 7 torr) weighed 61.3 g (87.6% of theory) and had a GC assay of 99.1%.

EXAMPLE 7

The procedure of Example 5 was repeated using tetra-n-heptylammonium chloride (3.0 g, 6.7 millimole) instead of tetraethylammonium chloride as catalyst. The distilled 3,4-dichloro-1,2-epoxybutane product (bp 30°–44° C., 1.5–2.3 torr) weighed 55.8 g (79.7% of theory) and had a GC assay of 99.3%.

COMPARATIVE EXAMPLE 1

To a 500-mL, four neck flask equipped with a gas addition tube, condenser, thermometer, mechanical stirrer, and cooling bath was added 200 mL of dichloromethane and 34.8 g (0.497 mole) of 3,4-epoxy-1-butene. The solution was cooled to −5° to 5° C. and then the addition of chlorine gas was begun. Chlorine (41.6 g, 0.587 mole) was added at −5° to 5° C. until the solution turned green. The mixture was washed with 100 mL of 10% aqueous sodium thiosulfate, then with 100 mL of half saturated aqueous sodium bicarbonate. The mixture was dried, filtered, and concentrated. The crude product was distilled at 7 torr to give a 3,4-dichloro-1,2-epoxybutane product fraction at 64°–66° C. The product weighed 4.57 g (theory 70.0 g, 6.53%) and had a GC assay of 89.1%.

COMPARATIVE EXAMPLE 2

To a 500-mL, four neck flask equipped with a gas addition tube, condenser, thermometer, mechanical stirrer, addition funnel, and cooling bath was added 200 mL of dichloromethane. The solution was cooled to −5° to 5° C. and then the chlorine gas addition was begun. After the solution had turned light green, 40 g (0.56 mole) of chlorine and 34.8 g (0.497 mole) of 3,4-epoxy-1-butene were added simultaneously over about 60 minutes at −5° to 5° C. so as to keep the solution green in color. The mixture was washed with 100 mL of 10% aqueous sodium thiosulfate and then with 100 mL of half saturated, aqueous sodium bicarbonate. The mixture was dried, filtered, and concentrated. The crude product was distilled at 7 torr to give a 3,4 dichloro 1,2 epoxy-butane product fraction at 58°–61° C. The colorless liquid weighed 22.3 g (31.9%) and had a GC assay of 98.0%.

The advantages afforded by the process of the present invention are shown in the Table wherein the results obtained in Examples 4–7 and Comparative Examples 1 and 2 are summarized. In the Table, Addition Mode refers to (i) the addition of chlorine to a mixture of 3,4-epoxy-1-butene, catalyst and solvent (Normal) or (ii) the addition of chlorine and 3,4-epoxy-1-butene to a mixture of chlorine, catalyst and solvent (Inverse); Catalyst refers to the presence or absence of a tetraalkylammonium chloride compound; Crude Assay is the GC area percent, disregarding solvent, of the crude product prior to distillation; and Distilled Yield is the yield of 3,4-dichloro-1,2-epoxybutane obtained by distillation based on the theoretical amount obtainable from the 3,4-epoxy-1-butene used.

TABLE

| Example | Addition Mode | Catalyst | Crude Assay | Distilled Yield |
| --- | --- | --- | --- | --- |
| 4 | Inverse | Yes | 93.5 | 81.1 |
| 5 | Normal | Yes | 83.9 | 66.0 |
| 6 | Inverse | Yes | 86.1 | 87.6 |
| 7 | Inverse | Yes | 92.3 | 79.7 |
| C-1 | Normal | No | 50.3 | 6.5 |
| C-2 | Inverse | No | 68.3 | 31.9 |

The invention has been described in detail with particular reference to preferred embodiments thereof, but it will be understood that variations and modifications can be effected within the spirit and scope of the invention.

We claim:

1. Process for the preparation of a compound having the formula

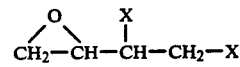

which comprises reacting 3,4-epoxy-1-butene and $X_2$ in the presence of a quaternary nitrogen or phosphorus onium halide compound having the formula

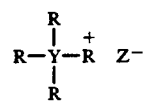

wherein each R is a hydrocarbyl group; X is Cl or Br; Y is a nitrogen or phosphorus atom; and Z is halogen.

2. Process according to claim 1 for the preparation of a compound having the formula

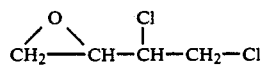

which comprises reacting 3,4-epoxy-1-butene and $Cl_2$ at a temperature of about 0° to 20° C. in the presence of a quaternary nitrogen or phosphorus onium chloride compound containing a total of about 8 to 32 carbon atoms and having the formula

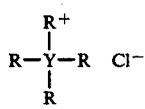

and an organic, halogenation solvent, wherein each R is a hydrocarbyl group and Y is a nitrogen or phosphorus atom.

3. Process according to claim 2 wherein the onium chloride is tetra-n-butylphosphonium chloride or tetraethylammonium chloride and the solvent is chlorobenzene or dichloromethane.

4. Process for the preparation of a compound having the formula

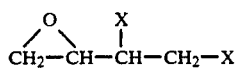

which comprises adding 3,4-epoxy-1-butene and $X_2$ to a solution of $X_2$ and a quaternary nitrogen or phosphorus onium halide compound having the formula

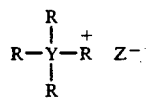

in an organic, halogenation solvent, wherein each R is a hydrocarbyl group; X is Cl or Br; Y is a nitrogen or phosphorus atom; and Z is halogen.

5. Process for the preparation of a compound having the formula

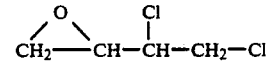

which comprises adding 3,4-epoxy-1-butene and $Cl_2$ to a solution of $Cl_2$ and a quaternary nitrogen or phosphorus onium halide compound containing a total of about 8 to 32 carbon atoms and having the formula

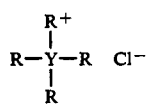

in an organic, halogenation solvent at a temperature of about 0° to 20° C., wherein each R is a hydrocarbyl group and Y is a nitrogen or phosphorus atom.

6. Process according to claim 5 wherein the onium chloride is tetra-n-butylphosphonium chloride or tetraethylammonium chloride and the solvent is chlorobenzene or dichloromethane.

* * * * *